United States Patent
Kitamura

(10) Patent No.: US 9,156,774 B2
(45) Date of Patent: Oct. 13, 2015

(54) CARBOXYLIC ACID ESTER COMPOUND AND METHOD FOR PRODUCING SAME, AND FRAGRANCE COMPOSITION

(75) Inventor: Mitsuharu Kitamura, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 199 days.

(21) Appl. No.: 14/007,456

(22) PCT Filed: Mar. 23, 2012

(86) PCT No.: PCT/JP2012/057524
§ 371 (c)(1),
(2), (4) Date: Dec. 5, 2013

(87) PCT Pub. No.: WO2012/133189
PCT Pub. Date: Oct. 4, 2012

(65) Prior Publication Data
US 2014/0087990 A1    Mar. 27, 2014

(30) Foreign Application Priority Data
Mar. 25, 2011 (JP) ................... 2011-067952

(51) Int. Cl.
C07C 69/753 (2006.01)
C11B 9/00 (2006.01)
A23L 1/20 (2006.01)
C07C 67/38 (2006.01)

(52) U.S. Cl.
CPC ............. *C07C 69/753* (2013.01); *A23L 1/2003* (2013.01); *C07C 67/38* (2013.01); *C11B 9/0046* (2013.01); *C11B 9/0053* (2013.01); *C07C 2102/44* (2013.01)

(58) Field of Classification Search
CPC ..................................... C11B 9/0053
USPC ...................... 512/22; 560/114, 118
See application file for complete search history.

(56) References Cited

U.S. PATENT DOCUMENTS

| | | | |
|---|---|---|---|
| 3,967,629 A * | 7/1976 | Chappell et al. ............. | 131/276 |
| 4,218,347 A | 8/1980 | Naf et al. | |
| 4,442,025 A | 4/1984 | Boelens et al. | |
| 4,843,061 A | 6/1989 | Broekhof et al. | |
| 2005/0119157 A1 | 6/2005 | Goeke | |

FOREIGN PATENT DOCUMENTS

| | | |
|---|---|---|
| JP | 50-63148 A | 5/1975 |
| JP | 54-052065 A | 2/1979 |
| JP | 57-021350 A | 2/1982 |
| JP | 60-152432 A | 8/1985 |
| JP | 60-190738 A | 9/1985 |
| JP | 62-298558 A | 12/1987 |
| JP | 2005-511819 A | 4/2005 |

OTHER PUBLICATIONS

International Search Report issued May 29, 2012 in PCT/JP2012/057524.
Takashi Nakajima, "Basics of fragrance and perfuming" Sangyo Tosho Co., 1995, 8 Pages.
Genichi Indoh, "Gosei Koryo, (Synthetic Fragrance)" Kagaku Kogyo Nippo Co., Ltd, (The Chemical Daily), Mar. 6, 1996, 16 Pages.

* cited by examiner

*Primary Examiner* — Ling Choi
*Assistant Examiner* — Lanee Reuther
(74) *Attorney, Agent, or Firm* — Oblon, McClelland, Maier & Neustadt, L.L.P.

(57) ABSTRACT

The present invention provides a novel carboxylic acid ester compound useful as a fragrance component or a material for a compound fragrance and a method for producing the same, and provides a fragrance composition including the carboxylic acid ester compound. The present invention also provides an acyl fluorides of a 2,4-dimethyl-bicyclo[2.2.2]octane compound and the esters thereof, useful as the raw materials (inclusive of the intermediates of organic synthesis), for example, for the medicines, agricultural chemicals, fragrances, functional resins, optical functional materials and electronic functional materials. The carboxylic acid ester compound of the present invention is a compound represented by the general formula (1).

[Formula 1]

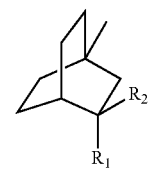

(1)

(In the formula, one of $R_1$ and $R_2$ is a methyl group and the other of $R_1$ and $R_2$ is —COOR, and R is an alkyl group having 1 to 4 carbon atoms.)

13 Claims, No Drawings

CARBOXYLIC ACID ESTER COMPOUND AND METHOD FOR PRODUCING SAME, AND FRAGRANCE COMPOSITION

TECHNICAL FIELD

The present invention relates to a novel carboxylic acid ester compound useful as a fragrance component or a material for a compound fragrance and a method for producing the same, and a fragrance composition including the carboxylic acid ester compound. The present invention also relates to the acyl fluorides of the 2,4-dimethyl-bicyclo[2.2.2]octane compounds and the esters thereof, useful as the raw materials (inclusive of the intermediates in organic synthesis), for example, for medicines, agricultural chemicals, fragrances, functional resins, optical functional materials and electronic functional materials.

BACKGROUND ART

It has hitherto been known that esters include compounds useful as fragrances. For examples, Non Patent Literature 1 describes the usefulness of the following esters as a material for a compound fragrance: geranyl acetate having rose-like aroma, methyl jasmonate having jasmine-like sweet aroma, fruitate having fruity aroma and methyl benzoate having intense dry fruity aroma.

CITATION LIST

Non Patent Literature

Non Patent Literature 1: "Basics of fragrance and perfuming," edited by Takashi Nakajima, 1995, p. 215, p. 235, and pp. 244-247, Sangyo Tosho Co.

SUMMARY OF INVENTION

Technical Problem

Recently, the preference of the consumers has been diversified, and the demands of the consumers have extended to the scent of products. For the purpose of coping with such diversification, the development of unprecedented fragrance components has been demanded.

The compounds having bulky ring structure such as norbornene and adamantane have been known as compounds useful as raw materials (inclusive of the intermediates in organic synthesis) for medicines, agricultural chemicals, functional resins, optical functional materials and electronic functional materials). Accordingly, in these applications, there has been requested the realization of novel compounds having such bulky ring structure.

The present invention has been achieved for the purpose of solving such problems, and an object of the present invention is to provide a novel carboxylic acid ester compound useful as a fragrance component or a material for a compound fragrance and a method for producing the novel carboxylic acid ester compound, and a fragrance composition including the carboxylic acid ester compound. Another object of the present invention is to provide the acyl fluorides of the 2,4-dimethyl-bicyclo[2.2.2]octane compounds and the esters thereof, useful as the raw materials (inclusive of the intermediates of organic synthesis), for example, for the medicines, agricultural chemicals, fragrances, functional resins, optical functional materials and electronic functional materials.

Solution to Problem

The present inventors made a diligent study for the purpose of solving such problems, synthesized various compounds and evaluated the properties of the resulting compounds, and consequently have reached the present invention by discovering that the carboxylic acid ester compounds, which are novel compounds, represented by the general formula (1) are useful as fragrance components or material for a compound fragrances. The present inventors have also reached the present invention by discovering that the acyl fluorides of the newly synthesized compounds, 2,4-dimethyl-bicyclo[2.2.2] octane compounds, and the esters thereof are effectively usable as the raw materials (inclusive of the intermediates in organic synthesis), for example, for medicines, agricultural chemicals, fragrances, functional resins, optical functional materials and electronic functional materials.

[Formula 1]

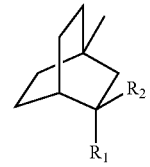

(1)

(In the formula, one of $R_1$ and $R_2$ is a methyl group, and the other of $R_1$ and $R_2$ is —COOR, and R is an alkyl group having 1 to 4 carbon atoms.)

Specifically, the present invention provides the following [1] to [3].

[1]
A carboxylic acid ester compound represented by the general formula (1).

[2]
The carboxylic acid ester compound according to the foregoing [1], represented by the general formula (1a).

[Formula 2]

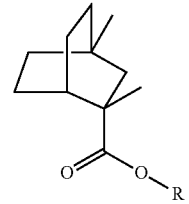

(1a)

(In the formula, R is an alkyl group having 1 to 4 carbon atoms.)

[3]
A fragrance composition including the carboxylic acid ester compound represented by the general formula (1).

[4]
A method for producing the carboxylic acid ester compound represented by the general formula (1) by allowing, in the presence of hydrogen fluoride, 4-isopropenyl-1-methyl-1-cyclohexene represented by the formula (2) to react with carbon monoxide and a monovalent alcohol having 1 to 4 carbon atoms.

[Formula 3]

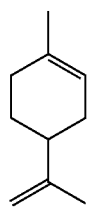
(2)

[Formula 4]

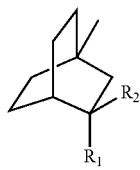
(1)

(In the formula, one of $R_1$ and $R_2$ is a methyl group and the other of $R_1$ and $R_2$ is —COOR, and R is an alkyl group having 1 to 4 carbon atoms.)

The present invention also provides the following [4].

[4]

A method for producing the acyl fluoride of 2,4-dimethyl-bicyclo[2.2.2]octane represented by the formula (3) by allowing, in the presence of hydrogen fluoride, 4-isopropenyl-1-methyl-1-cyclohexene represented by the formula (2) to react with carbon monoxide.

[Formula 5]

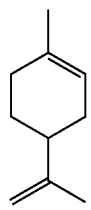
(2)

[Formula 6]

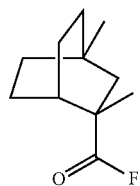
(3)

Advantageous Effects of Invention

According to the present invention, a novel carboxylic acid ester compound is provided which is novel in the aspects of physical properties in such a way that the novel carboxylic acid ester compound has an intense aroma provided both with a fruity aroma and with a spicy, rose-like floral feeling recalling damascone, and is relatively excellent in aroma sustainability. The present invention also enables the production of such a novel carboxylic acid ester compound by an industrially favorable method, and hence enhances the economic efficiency and the productivity. The use of such a carboxylic acid ester compound as a fragrance imparting component or as a material for a compound fragrance enables the diversification of fragrance in a wide variety of products such as perfumery and cosmetics, health and sanitary materials, convenience goods, fiber, fiber products, clothing, food, quasi-pharmaceutical products and medicinal supplies. Furthermore, the present invention provides a novel 2,4-dimethyl-bicyclo[2.2.2]octane compound useful as a raw material (inclusive of the intermediates in organic synthesis) for medicines, agricultural chemicals, fragrances, functional resins, optical functional materials and electronic functional materials.

DESCRIPTION OF EMBODIMENT

Hereinafter, the embodiments of the present invention are described. The following embodiments are exemplification for describing the present invention, and the present invention is not limited only to the embodiments thereof.

[Novel Carboxylic Acid Ester Compound Represented by General Formula (1)]

The novel carboxylic acid ester compound of the present embodiment is a compound represented by the general formula (1).

[Formula 7]

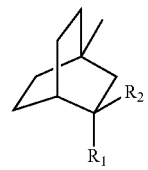
(1)

(In the formula, one of $R_1$ and $R_2$ is a methyl group and the other of $R_1$ and $R_2$ is —COOR, and R is an alkyl group having 1 to 4 carbon atoms.)

Examples of the alkyl group having 1 to 4 carbon atoms in the general formula (1) include a linear alkyl group and a branched alkyl group. Specific examples of such alkyl groups include, without being particularly limited to, a methyl group, an ethyl group, an n-propyl group, an iso-propyl group, an n-butyl group, an iso-butyl group and a tert-butyl group. Among these, R is preferably an ethyl group and an iso-propyl group.

As the carboxylic acid ester compound represented by the foregoing general formula (1), the following isomers can exist; however, the carboxylic acid ester compound represented by the general formula (1) may be a single substance, namely, one of these isomers, or may be a mixture composed of these isomers in any proportions.

[Formula 8]

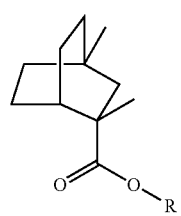
(1a)

(In the formula, R represents an alkyl group having 1 to 4 carbon atoms.)

[Formula 9]

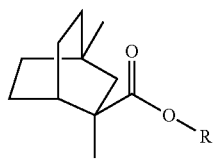

(1b)

(In the formula, R represents an alkyl group having 1 to 4 carbon atoms.)

[Method for Producing Novel Carboxylic Acid Ester Compound]

A preferable method for producing the carboxylic acid ester compound represented by the general formula (1) is a synthesis method based on the following reaction path. The synthesis method based on such a reaction path is an industrially favorable method, and hence the adoption of the synthesis method particularly enhances the economic efficiency and the productivity. Hereinafter, such a preferable synthesis method is described in detail.

[Formula 10]

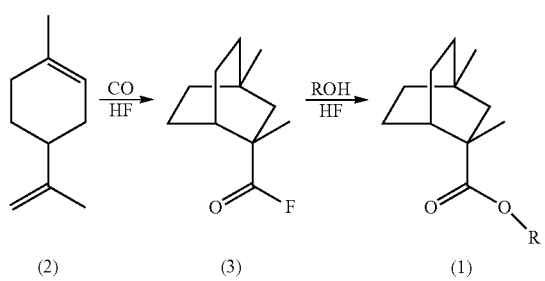

In the synthesis method, the carboxylic acid ester compound represented by the general formula (1) is synthesized by performing the following first and second stage reactions: the first stage reaction (hereinafter, also simply referred to as "the carbonylation reaction") for obtaining the acyl fluoride of the 2,4-dimethyl-bicyclo[2.2.2]octane compound represented by the formula (3) by using the compound represented by the formula (2) as a starting material, and by allowing the compound represented by the formula (2) to react with carbon monoxide in the presence of hydrogen fluoride to mainly perform the cyclization and the carbonylation of the compound represented by the formula (2); and the second stage reaction (hereinafter, also simply referred to as "the esterification reaction") for performing esterification by allowing the resulting acyl fluoride represented by the formula (3) to react with an alcohol.

[Compound Represented by the Formula (2)]

The compound represented by the formula (2) is 4-isopropenyl-1-methyl-1-cyclohexene (generic name: limonene). As 4-isopropenyl-1-methyl-1-cyclohexene, there exist three types of species, namely, the d-isomer, l-isomer and d/l-isomer (dipentene), and any of these can be used. Limonene is abundantly contained in the natural essential oil obtained from the rind of orange, lemon or grapefruit, and hence can be obtained as a product of 98% in purity by steam distillation. Limonene is also used in other applications and industrially produced, and hence can be available at low prices.

[Hydrogen Fluoride]

The hydrogen fluoride (hereinafter, also simply described as "HF") used in the carbonylation reaction functions as a solvent and a catalyst in the carbonylation reaction, and also serves as an auxiliary raw material, and hence is preferably substantially anhydrous (anhydrous hydrogen fluoride or anhydrous hydrofluoric acid). The amount used of HF can be appropriately set according to need without being particularly limited; however, the amount used of HF is preferably 3 to 25 times, and more preferably 8 to 15 times the number of moles of the compound represented by the formula (2) which serves as a main raw material. The molar ratio of HF set at 3 times or more and 25 times or less allows the carbonylation reaction to proceed efficiently, suppresses its side reaction such as disproportionation or polymerization, and allows the target carbonyl compound to tend to be obtained in a high yield.

[Carbon Monoxide]

As the carbon monoxide used in the carbonylation reaction, the well-known carbon monoxide gas distributed as the common industrial gas can be appropriately used, without being particularly limited. For example, the carbon monoxide gas to be used may contain, for example, an inert gas such as nitrogen or methane. The above-described carbonylation reaction is performed under the carbon monoxide partial pressure set preferably within a range from 0.5 to 5.0 MPa and more preferably within a range from 1.0 to 3.0 MPa. The carbon monoxide partial pressure set at 0.5 MPa or more allows the carbonylation reaction to proceed sufficiently and suppresses the side reaction such as disproportionation or polymerization, and allows the target alicyclic carbonyl compound to tend to be obtained in a high yield. The carbon monoxide partial pressure set at 5 MPa or less allows the load exerted on the reaction system (apparatus) to tend to be reduced.

[Solvent]

In the carbonylation reaction, a solvent dissolving the raw material and being inert to HF may be used. Examples of such a solvent include, without being particularly limited to, saturated hydrocarbon compounds such as hexane, heptane and decane. The use or nonuse of a solvent and the amount used of the solvent may be appropriately set in consideration of other reaction conditions and are not particularly limited. From the viewpoint of the enhancement of the yield by suppressing the polymerization reaction, the amount used of the solvent is preferably 0.2 to 2.0 times by mass the amount of the compound, the main raw material, represented by the formula (2), and from the viewpoint of the productivity and the energy efficiency, the amount used of the solvent is preferably 0.5 to 1.0 times by mass the amount of the compound, the main raw material, represented by the formula (2).

[Alcohol]

In the carbonylation reaction, an alcohol can also be used. An alcohol is preferably added to suppress the side reaction in the carbonylation reaction, as an esterification agent at the time of the step of the carbonylation reaction. Examples of the alcohol usable herein include methanol, ethanol, n-propanol, iso-propanol, n-butanol, iso-butanol and tert-butanol. The use or nonuse of an alcohol and the amount used of the alcohol in the carbonylation reaction may be appropriately set in consideration of other reaction conditions and are not particularly limited; however, the amount used of the alcohol is preferably 0.1 to 0.9 times, and more preferably 0.2 to 0.7 times the number of moles of the compound, the main raw material, represented by the formula (2). The molar ratio of the alcohol set within a range from 0.1 to 0.9 times the number of moles of the compound represented by the formula (2) allows the carbonylation reaction to proceed sufficiently and suppresses the side reaction such as disproportionation or polymerization, and allows the target alicyclic carbonyl compound (acyl fluoride) in the step to tend to be obtained in a high yield.

[Carbonylation Reaction Conditions]

The reaction temperature in the carbonylation reaction is not particularly limited, but is preferably −50° C. to 30° C. and more preferably −30° C. to 20° C., from the viewpoint of increasing the yield by increasing the reaction rate and suppressing the side reaction and additionally, obtaining the high-purity target product. The reaction time is not particularly limited, but is preferably 1 to 5 hours, from the viewpoint of allowing the carbonylation reaction to proceed sufficiently and increasing the efficiency. The carbonylation reaction is preferably performed under pressurized conditions from the viewpoint of increasing the reaction efficiency. The carbonylation reaction is preferably performed under normal pressure or under pressurized conditions, namely, under a pressure of 1.0 to 5.0 MPa, and more preferably at 1 to 3 MPa, from the viewpoint of increasing the reaction efficiency and reducing the equipment burden. The type of the carbonylation reaction is not particularly limited, and may be any of, for example, a batch-type reaction, a semi-continuous type reaction and a continuous type reaction. The end point of the reaction is not particularly limited, but may be determined with reference to the time at which no absorption of carbon monoxide is recognized any more.

The above-described carbonylation reaction yields a mixed solution (carbonylation reaction product solution) including the acyl fluoride, the reaction product (intermediate) represented by the formula (3) and additionally, hydrogen fluoride, and according to need, for example, the solvent, the alcohol, and the like.

Successively, the produced alicyclic carbonyl compound (acyl fluoride), represented by the formula (3) is allowed to react with an alcohol in the presence of HF to yield the carboxylic acid ester represented by the general formula (1). The esterification reaction can be performed, by adding an alcohol in the presence of HF after the produced acyl fluoride, represented by the formula (3), is once isolated and purified from the foregoing carbonylation reaction product solution according to a conventional method; and alternatively, the esterification reaction can also be performed continuously from the foregoing carbonylation reaction by further adding HF and/or an alcohol to the foregoing carbonylation reaction product solution.

The preferable amount used of HF in the esterification reaction is the same as described for the carbonylation reaction, and hence the duplicative description is omitted.

Examples of the alcohol as an auxiliary raw material used in the esterification include the same alcohols as described for the carbonylation reaction, namely, the monovalent alcohols such as methanol, ethanol, n-propanol, iso-propanol, n-butanol, iso-butanol and tert-butanol. The amount used of the alcohol in the esterification reaction is preferably such that the total amount of the alcohols used in the carbonylation reaction and the esterification reaction is 1.0 to 2.0 times the number of moles of the compound, the main raw material, represented by the formula (2), from the viewpoint of increasing the reaction efficiency and obtaining the high-purity target product. The amount used of the alcohol in the esterification reaction set within such a range reduces the amount of the unreacted acyl fluoride remaining in the reaction product, and tends to suppress the degradation of the product purity due to the acyl fluoride remaining in the reaction product together with the target ester compound and on the other hand, the remaining proportion of the unreacted alcohol is reduced and the separation (isolation) of the obtained target product is facilitated, and hence the product purity tends to be increased.

The amount used of the alcohol set within the foregoing preferable range tends to alleviate the following problems (1) and (2) due to the accumulation of water in the recovered HF because the water is by-produced by the dehydration reaction of the unreacted alcohol and the water is azeotropically distilled with HF.

(1) A problem of an adverse effect on the reaction
(2) A problem of remarkable corrosion of the equipment materials Here, from the viewpoint of attaining a high yield, alcohol is preferably added in a predetermined amount in each of the carbonylation reaction and the esterification reaction. In this case, it is more preferable that in the carbonylation reaction, the amount used of the alcohol be set to be 0.1 to 0.5 times the number of moles of the compound, the main raw material, represented by the formula (2), and in the esterification reaction, the amount used of the alcohol is further added in such a way that the total amount of the alcohol, inclusive of the amount added in the carbonylation reaction, is set to be 1.0 to 2.0 times the number of moles of the compound, the main raw material, represented by the formula (2). From the viewpoint of efficiently isolating the obtained target product, the alcohol used in the esterification reaction and the alcohol optionally used in the carbonylation reaction are preferably the same as each other.

[Esterification Reaction Conditions]

The reaction temperature in the esterification reaction is not particularly limited, but is preferably −20° C. or higher and 20° C. or lower, from the viewpoint of suppressing the side reaction and increasing the yield, and from the viewpoint of suppressing the by-production of water due to the dehydration reaction of the added alcohol. The reaction time is not particularly limited, but is preferably 0.5 to 3 hours from the viewpoint of allowing the esterification reaction to proceed sufficiently and increasing the efficiency. The esterification reaction is preferably performed under pressurized conditions from the viewpoint of increasing the reaction efficiency. The esterification reaction is preferably performed under normal pressure or under pressurized conditions, namely, under a pressure of 0.1 to 5.0 MPa, and more preferably at 1 to 3 MPa, from the viewpoint of increasing the reaction efficiency and reducing the equipment burden. The type of the esterification reaction is not particularly limited, and may be any of, for example, a batch-type reaction, a semi-continuous type reaction and a continuous type reaction. The end point of the reaction is not particularly limited, but may be determined with reference to the time at which no increase of the heat of reaction is recognized any more.

The foregoing esterification reaction yields a mixed solution (esterification reaction product solution) including the carboxylic acid ester compound represented by the general formula (1), HF and if necessary, for example, the solvent and the alcohol. The esterification reaction product solution can include the complex between the carboxylic acid ester compound represented by the general formula (1) and HF; however, HF can be separated by gasification, recovered and reused by decomposing the bonding between the carboxylic acid ester compound represented by the general formula (1) and HF. The decomposition operation of the complex is preferably performed as quickly as possible, from the viewpoint of suppressing, for example, the thermal deterioration or the isomerization of the product. For the purpose of allowing the thermal decomposition of the complex to proceed rapidly, it is preferable to heat the esterification reaction product solution, for example, under the reflux of a solvent inert to HF (for example, a saturated aliphatic hydrocarbon such as heptane or an aromatic hydrocarbon such as benzene).

The isolation of the carboxylic acid ester compound represented by the general formula (1) can be performed according to a conventional method, and the method is not particularly limited. For example, the esterification reaction product solution is extracted in iced water and separated into the oil phase and the aqueous phase; then the oil phase is washed alternately with a sodium hydroxide aqueous solution and distilled water, and dehydrated with anhydrous sodium sulfate; from the dehydrated oil phase, for example, low boiling-point substances are removed with an evaporator; then, by rectifying the oil phase with a rectifying column having a number of theoretical plates of 20 or more, the carboxylic acid ester compound represented by the general formula (1) can be obtained with a relatively high purity.

The carboxylic acid ester compound represented by the general formula (1) obtainable in this way has an intense aroma provided both with a fruity aroma and with a spicy, rose-like floral feeling recalling damascone, and is relatively excellent in aroma sustainability; accordingly, as a fragrance component (fragrance imparting component) or a material for a compound fragrance, the carboxylic acid ester compound can be effectively used in various applications, for example, in perfumery and cosmetics, health and sanitary materials, convenience goods, fiber, fiber products, clothing, food, quasi-pharmaceutical products and medicinal supplies. The carboxylic acid ester compound represented by the general formula (1) can also be effectively used as a raw material (inclusive of the intermediates in organic synthesis), by taking advantage of the bulky ring structure, rigidity, optical transparency, high Tg and lubricity (liposolubility) of 2,4-dimethyl-bicyclo[2.2.2]octane, for example, for medicines, agricultural chemicals, functional resins, and optical functional materials and electronic functional materials such as liquid crystals and resists.

[Fragrance Composition]

The fragrance composition of the present embodiment includes the novel carboxylic acid ester compound represented by the general formula (1). The fragrance composition of the present embodiment may include any other components as long as the fragrance composition includes the novel carboxylic acid ester compound represented by the general formula (1). For example, the fragrance composition of the present embodiment may include, as another component, a fragrance component (fragrance imparting component) other than the novel carboxylic acid ester compound represented by the general formula (1).

As the foregoing other fragrance components, there have been known, for example, aldehydes, phenols, alcohols, ethers, esters, hydrocarbons, ketones, lactones, musks, fragrances having a terpene skeleton, natural fragrances, natural essential oils, plant extracts and animal fragrances; various fragrance components are described, for example, in Koryo Kagaku Soran (Fragrance Chemistry Comprehensive Bibliography) 1, 2, 3, (by Osamu Okuda, published by Hirokawa Shoten), Gosei Koryo (Synthetic Fragrance) (by Genichi Indoh, Published by Kagaku Kogyo Nippo (The Chemical Daily) Co., Ltd.), and "Patent Office Gazette, Collection of Well-known Prior Arts, Part III, Perfumes, pp. 26-103, published on Jun. 15, 2001."

Specific examples of such fragrance components include, without being particularly limited to: surfactants such as polyoxyethylene lauryl sulfate ether; solvents such as dipropylene glycol, diethyl phthalate, ethylene glycol, propylene glycol, methyl myristate and triethyl citrate; hydrocarbons such as limonene, α-pinene, β-pinene, terpinene, cedrene, longifolene and valencene; alcohols such as linalool, citronellol, geraniol, nerol, terpineol, dihydromyrcenol, ethyl linalool, farnesol, nerolidol, cis-3-hexenol, cedrol, menthol, borneol, β-phenylethylalcohol, benzylalcohol, phenylhexanol, 2,2,6-trimethylcyclohexyl-3-hexanol, 1-(2-t-butylcyclohexyloxy)-2-butanol, 4-isopropylcyclohexanemethanol, 4-methyl-2-(2-methylpropyl)tetrahydro-2H-pyran-4-ol, 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, isocamphylcyclohexanol, 3,7-dimethyl-7-methoxyoctan-2-ol; phenols such as eugenol, thymol and vanillin; esters such as linalylformate, citronellylformate, geranylformate, n-hexylacetate, cis-3-hexenylacetate, linalylacetate, citronellylacetate, geranylacetate, nerylacetate, terpinylacetate, nopylacetate, bornylacetate, isobornylacetate, o-t-butylcyclohexylacetate, p-t-butylcyclohexylacetate, tricyclodecenylacetate, benzylacetate, styrallylacetate, cinnamylacetate, dimethylbenzylcarbynylacetate, 3-pentyltetrahydropyran-4-ylacetate, citronellylpropionate, tricyclodecenylpropionate, allylcyclohexylpropionate, ethyl 2-cyclohexylpropionate, benzylpropionate, citronellylbutyrate, dimethylbenzylcarbynyl n-butyrate, tricyclodecenylisobutyrate, methyl 2-nonenoate, methylbenzoate, benzylbenzoate, methylcinnamate, methylsalicylate, n-hexylsalicylate, cis-3-hexenylsalicylate, geranyltiglate, cis-3-hexenyltiglate, methyljasmonate, methyldihydrojasmonate, methyl-2,4-dihydroxy-3,6-dimethylbenzoate, ethylmethylphenyl glycidate, methylanthranilate, fruitate; aldehydes such as n-octanal, n-decanal, n-dodecanal, 2-methylundecanal, 10-undecenal, citronellal, citral, hydroxycitronellal, dimethyltetrahydrobenzaldehyde, 4(3)-(4-hydroxy-4-methylpentyl)-3-cyclohexene-1-carboaldehyde, 2-cyclohexylpropanal, p-t-butyl-α-methylhydro cinnamic aldehyde, p-isopropyl-α-methylhydro cinnamic aldehyde, p-ethyl-α,α-dimethylhydro cinnamic aldehyde, α-amyl cinnamic aldehyde, α-hexyl cinnamic aldehyde, piperonal, α-methyl-3,4-methylenedioxyhydro cinnamic aldehyde; ketones such as methylheptenone, 4-methylene-3,5,6,6-tetramethyl-2-heptanone, amylcyclopentanone, 3-methyl-2-(cis-2-penten-1-yl)-2-cyclopenen-1-one, methylcyclopentenone, rose ketone, γ-methylonone, α-ionone, carvone, menthone, camphor, nootkatone, benzylacetone, anisylacetone, methyl β-naphthyl ketone, 2,5-dimethyl-4-hydroxy-3(2H)-furanone, maltol, 7-acetyl-1,2,3,4,5,6,7,8-octahydro-1,1,6,7-tetramethylnaphthalene, muskon, civetone, cyclopentadecanone and cyclohexadecenone; acetals and ketals such as acetaldehyde ethylphenylpropylacetal, citral diethylacetal, phenylacetaldehyde glycerinacetal, ethylacetoacetate ethyleneglycol ketals; ethers such as anethole, β-naphthyl methyl ether, β-naphthyl ethyl ether, limonene oxide, rose oxide, 1,8-cineol, and racemic or optically active dodecahydro-3a,6,6,9a-tetramethylnaphtho[2,1-b]furan; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate and 11-oxahexadecanolide; natural essential oils and natural extracts of orange, lemon, bergamot, mandarin, peppermint, spearmint, lavender, chamomile, rosemary, eucalyptus, sage, basil, rose, geranium, jasmine, ylang ylang, anise, clove, ginger, nutmeg, cardamon, cedar, hinoki cypress, vetiver, patchouli and labdanum. These can be used each alone or in combinations of two or more thereof.

The fragrance composition of the present embodiment may include, if necessary, in addition to these fragrance components, various additives (not functioning as fragrance components) used, for example, in perfumery and cosmetics, health and sanitary materials, convenience goods, fiber, fiber products, clothing, food, quasi-pharmaceutical products and medicinal supplies. Specific examples of the various additives include, without being particularly limited to: solvents, dispersion media, fine particles (powder), liquid oils and fats, solid oils and fats, wax, oil-soluble components, silicones, hydrocarbons, higher fatty acids, higher alcohols, lower alcohols, polyhydric alcohols, esters, glycols, alcohol ethers, saccharides, amino acids, organic amines, polymer emulsions, pH adjusters, skin nutrients, vitamins, anionic surfactants, cationic surfactants, amphoteric surfactants, nonionic surfactants, ultraviolet absorbers, oil-gelling agents, moisturizers, aqueous components, propellants, antioxidants, antioxidant aids, cosmetic ingredients, preservatives, water-soluble polymers, water, film-forming ingredients, anti-fading agents, fragrance retainers, thickeners, antifoaming agents, disinfectants, deodorants, dyes, pigments, pearlizing agents, chelate agents and gelling agents. These can be used each alone or in combinations of two or more thereof.

The fragrance composition of the present embodiment can be used in any forms, according to the properties of the fragrance-accepting component and the various additives mixed if necessary, and the form of use thereof is not particularly limited. The fragrance composition of the present embodiment can be used in liquid-like, gel-like, semi-solid-like, jelly-like, solid-like, powder-like, mist-like, aerosol-like, emulsion-like and suspension-like forms. The fragrance composition of the present embodiment can also be used in the forms sprayed to, applied to, adsorbed on, mixed with, dispersed in, emulsified in, kneaded with, supported on, penetrating in or impregnated into base materials such as yarns, woven knitted goods, woven fabric, non-woven fabric, organic and inorganic fibers such as papers, resins, clothing materials and clothing. Moreover, the fragrance composition of the present embodiment can be imparted to fragrance-accepting components by using, for example, microcapsules. The carboxylic acid ester compound represented by the general formula (1) and the fragrance composition of the present embodiment allow the fragrance thereof to be sprayed or diffused by using a diffuser.

The content of the carboxylic acid ester compound represented by the general formula (1) in the fragrance composition of the present embodiment can be appropriately set, without being particularly limited, according to, for example, the intended type and intensity of aroma, the type and the amount of the other fragrance component used in combination, the intended aroma sustainability and the form of use; however, the content of the foregoing carboxylic acid ester compound is preferably 0.01 to 90% by mass and more preferably 0.1 to 50% by mass in relation to the total amount of the fragrance composition.

[Applications]

The carboxylic acid ester compound represented by the general formula (1), unlike the heretofore known fruitate having only fruity aroma or heretofore known geranyl acetate having only rose-like aroma, has a novel aroma intensely provided both with a fruity aroma and with a spicy, rose-like floral feeling recalling damascone and is excellent in aroma sustainability as compared to other heretofore known esters or geranyl acetate; accordingly, the foregoing carboxylic acid ester compound can be used widely alone as the fragrance component (fragrance imparting component) or a material for a compound fragrance, in various products such as perfumery and cosmetics, health and sanitary materials, convenience goods, fiber, fiber products, clothing, food, quasi-pharmaceutical products and medicinal supplies, and can also be used for improving the aroma of an object with which fragrance is mixed.

Specific examples of the various products include fragrance products, basic skin-care products, make up cosmetic, hair care and cosmetic products, hair cosmetics, skin care cosmetics, anti-sunburn cosmetics, medicinal cosmetics, soaps, body cleaners, bath water additives, detergents, softener, bleach, disinfectant detergents, deodorant detergents, furniture care agents, various cleaning agents, glass cleaners, furniture cleaners, floor cleaners, disinfectants, insecticides, bleaches, aerosols, deodorants, aromatics, deodorant aromatics, repellents and other miscellaneous goods.

More specifically, examples of the various products include: perfume, parfum, eau de parfum, eau de toilette, colognes, fragrance powder, solid perfume, shampoo, conditioners, rinse, rinse in shampoo, hair tonic, hair creams, brilliantine, setting lotion, hair stick, solid hair dressing, hair oil, hair mousse, hair gel, hair pomade, hair liquid, hair spray, hair colorant, hair pack, hair growth pilatory, hair dye, lotion, milky lotion, body lotion, body powder, body soap, hand soap, hand cream, body cream, aroma oil, serum, cream, milky lotion, pack, foundation, face powder, lipstick, cleansing foam, cleansing cream, make-up remover, pack, vanishing cream, cleansing cream, cold cream, massage cream, oil blotting paper, foundation, eyeshadow, eyeliner, mascara, lipstick, make-up base, powder, pressed face powder, talcum powder, lip cream, cheek rouge, eyebrow pencil, eye pack, nail enamel, enamel remover, toilet soap, bath soap, perfume soap, transparent soap, synthetic soap, liquid soap, bath salt, bath tublet, bath liquid, bath foam, bath oil, bath capsule, milk bath, bath jelly, bath cube, antiperspirant, lip cream, shaving foam, after-shaving lotion, shaving gel, hair growth lotion, permanent wave lotion, medicinal soap, medicinal shampoo, medicinal skin cosmetic, dish washing detergent, kitchen detergent, table ware detergent, laundry detergent, clothing heavy duty detergent, clothing light duty detergent, liquid detergent, compact detergent, powder soap, softeners, furniture care agent, disinfectant detergents, deodorant detergents, drainage pipe detergent, oxidation-type bleach, reduction-type bleach, optical bleach, aerosols, solid/gel/liquid-form deodorant, solid/gel/liquid-form aromatic, solid/gel/liquid-form deodorant aromatic, cleanser, glass cleaner, furniture cleaner, leather cleaner, floor cleaner, house cleaner, fiber detergent, leather detergent, toilet detergent, bath detergent, glass cleaner, fungus-removing agent, furniture care agent, glass cleaner, furniture cleaner, floor cleaner, disinfectant, insecticide, toothpaste, mouthwash, bath water additive, antiperspirant, suntan cream, perm solution, depilatory, salve, cataplasm, ointment, patch, hair growth tonic, mouthwash, toilet paper, tissue paper, fragrance paper, room fragrance, aroma candle and aroma oil.

The amount used of each of these various products can be set appropriately, without being particularly limited, according to the target type of aroma and target intensity of aroma, the type and the amount of another fragrance component used in combination, the intended aroma sustainability, the use form and the use environment; however, the amount used of each of these various products is preferably 0.001 to 50% by mass and more preferably 0.01 to 20% by mass, in terms of the carboxylic acid ester compound represented by the general formula (1).

EXAMPLES

Hereinafter, the present invention is described in more detail with reference to Examples, but the present invention is not limited to these Examples. It is to be noted that hereinafter the term "parts" means "parts by mass," unless otherwise specified.

Hereinafter, the measurement methods in Examples are described.

<Gas Chromatograph Analysis Conditions>

Gas chromatograph was performed by using the gas chromatograph GC-17A manufactured by Shimadzu Corp. and the capillary column ULBON HR-1 (0.32 mmφ×25 m×0.50 µm) manufactured by Shinwa Chemical Industries Ltd. The temperature increase conditions were such that the temperature was increased from 100° C. to 300° C. at a temperature increase rate of 5° C./min.

Detector: FID (detector temperature: 310° C.)

Column: HR-1 Capillary column

Column temperature: 100° C. (temperature increase rate: 5° C./min)

Carrier gas: $N_2$ (flow rate: 1.8 mL/min)

Sample injection temperature: 310° C.

Sample injection amount: 0.2 µL, injection inlet temperature: 310° C.

Retention time: 0 min

<Yield and Isomer Ratio of Carboxylic Acid Ester Compound>

On the basis of the gas chromatograph analysis, the area proportions (GC %) of the compound represented by the formula (4), a target product, and an isomer thereof as a by-product (the isomer is not included in the compound represented by the formula (4)) were determined. Hereinafter, the mixture composed of the compound represented by the formula (4) and the isomer thereof is also referred to as "the isomer-containing carboxylic acid ester compound."

Subsequently, on the basis of an internal standard method, the yield of the compound represented by the formula (4) and the yield of the isomer-containing carboxylic acid ester compound were respectively determined, and then, the yield of the carboxylic acid ester compound represented by the formula (4) and the isomer ratio were respectively determined on the basis of the following formulas.

(Yield)

> Yield (mol %) of isomer-containing carboxylic acid ester compound=100×(total acquisition mass of isomer-containing carboxylic acid ester compound/210.3)/(feed mass of compound represented by the formula (2)/136.2) Yield (mol %) of compound represented by the formula (4)=100×(acquisition mass of compound represented by the formula (4)/210.3)/(feed mass of compound represented by the formula (2)/136.2)

(Isomer Ratio)

> Isomer ratio (%)=100×area proportion (GC %) of compound represented by the formula (4)/area proportion (GC %) of isomer-containing carboxylic acid ester compound

<GC-MS>

GC-MS analysis was performed by using the GC-MS spectrometer POLARIS Q manufactured by Thermo ELECTRON Corp.

<$^1$H-NMR Spectrum Analysis>

$^1$H-NMR spectra were measured by using the $^1$H-NMR spectrometer EX-270 BRUKER AVANCEII 600 manufactured by JEOL Ltd. (internal standard substance: tetramethylsilane (TMS)).

Example 1

Method for Synthesizing a Novel Compound, 2,4-dimethyl-bicyclo[2.2.2]octane-2-carboxylic acid ethyl ester

[Formula 11]

An experiment was performed by using a stainless steel autoclave having an internal volume of 500 ml, being equipped with a magnet drive type stirrer, three inlet nozzles in the top thereof and one extraction nozzle in the bottom thereof, and being capable of regulating the internal temperature with the aid of a jacket.

First, the air inside the autoclave was replaced with carbon monoxide, then 160 g (8.0 mol) of anhydrous hydrogen fluoride was introduced into the inside of the autoclave, the liquid temperature was set at −30° C., and then the inside of the autoclave was pressurized to 2.0 Mpa with carbon monoxide.

Successively, while the temperature inside the autoclave was being maintained at −30° C. and the pressure inside the autoclave was being maintained at 2.0 MPa, a mixed solution composed of 72.6 g (0.53 mol) of 4-isopropenyl-1-methyl-1-cyclohexene, 48.4 g of heptane and 6.1 g (0.13 mol) of ethanol was fed from the top of the autoclave; after the completion of the feeding of the raw materials, the stirring of the reaction mixture was continued for 1 hour until the absorption of carbon monoxide was not found any more (the carbonylation reaction step).

Next, following the carbonylation reaction, under the condition of 2.0 MPa, the temperature inside the autoclave was decreased; while the temperature inside the autoclave was being maintained at 0° C., 30.7 g (0.67 mol) of ethanol was fed from the top of the autoclave; after the completion of the feeding of the raw material, the reaction mixture was continuously stirred for 1 hour (the esterification reaction step).

Subsequently, the reaction product solution was extracted from the bottom of the autoclave into iced water, the oil phase and the aqueous phase were allowed to be separated, then the oil phase was collected, the oil phase was washed twice with 100 ml of a 2% by mass sodium hydroxide aqueous solution and twice with 100 ml of distilled water, and further, the oil phase was dehydrated with 10 g of anhydrous sodium sulfate. A sample was taken from the finally obtained solution, and by using the sample, a gas chromatograph analysis was performed on the basis of an internal standard method.

Consequently, the yield of the isomer-containing carboxylic acid ester compound was found to be 33.2 mol % (with reference to 4-isopropenyl-1-methyl-1-cyclohexene), and the yield of the compound represented by the formula (4), identified by the below-described GC-MS analysis and $^1$H-NMR spectrum analysis, namely, 2,4-dimethyl-bicyclo[2.2.2]octane-2-carboxylic acid ethyl ester was found to be 17.8 mol % (with reference to 4-isopropenyl-1-methyl-1-cyclohexene). The isomer ratio was found to be 53.6%.

After the low boiling-point substance was removed from the obtained solution with an evaporator, the obtained solution was rectified (distillation temperature: 164° C., degree of vacuum: 60 torr) with a rectifying column having a number of theoretical plates of 20, and consequently, a main distillation fraction of 53.3 GC % in terms of gas chromatograph analysis was obtained in an amount of 33.4 g (distillation yield: 90.0 mol %).

The rectified solution was further rectified with a rectifying column having a number of theoretical plates of 50 to isolate the main product. The obtained fraction has been verified as follows:

(1) the obtained fraction, unlike the heretofore known fruitate having only fruity aroma or heretofore known geranyl acetate having only rose-like aroma, has an intense aroma provided both with a fruity aroma and with a spicy, rose-like floral feeling recalling damascone; and (2) the obtained fraction is excellent in aroma sustainability as compared to other heretofore known esters or geranyl acetate.

The target product was analyzed with a GC-MS, and consequently the molecular weight of the target product was found to be 210.3.

The chemical shift values (δ ppm, with reference to TMS) of the $^1$H-NMR in a heavy chloroform solvent were found to be: 1.16 (s, 3H), 1.24 (m, 2H), 1.27 (m, 2H), 1.30 (t, 3H), 1.34 (s, 3H), 1.49 (m, 2H), 1.52 (m, 2H), 1.54 (s, 1H), 1.79 (s, 1H), 2.05 (m, 1H) and 4.12 (m, 2H).

From the above-described results, the obtained fraction was identified as 2,4-dimethyl-bicyclo[2.2.2]octane-2-carboxylic acid ethyl ester represented by the formula (4).

Example 2

The carbonylation reaction step, the esterification reaction step and the treatment of the reaction product solution were performed in the same manner as in Example 1 except that the carbonylation reaction step was performed at −25° C.

The obtained solution was analyzed with gas chromatography, and consequently, the yield of the isomer-containing carboxylic acid ester compound was found to be 36.9 mol % (with reference to 4-isopropenyl-1-methyl-1-cyclohexene), and the yield of the compound represented by the formula (4) was found to be 17.8 mol % (with reference to 4-isopropenyl-1-methyl-1-cyclohexene). The isomer ratio was found to be 48.2%.

Example 3

The carbonylation reaction step, the esterification reaction step and the treatment of the reaction product solution were performed in the same manner as in Example 1 except that the carbonylation reaction step was performed under pressurized conditions, namely, under 1.5 MPa of carbon monoxide.

The obtained solution was analyzed with gas chromatography, and consequently, the yield of the isomer-containing carboxylic acid ester compound was found to be 36.3 mol % (with reference to 4-isopropenyl-1-methyl-1-cyclohexene), and the yield of the compound represented by the formula (4) was found to be 17.4 mol % (with reference to 4-isopropenyl-1-methyl-1-cyclohexene). The isomer ratio was found to be 47.9%.

Example 4

Apricot-Type Fragrance Composition

First, the fragrance composition (control substance) having the composition shown in Table 1 was prepared. Next, to 90 parts by mass of the control substance, 10 parts by mass of 2,4-dimethyl-bicyclo[2.2.2]octane-2-carboxylic acid ethyl ester represented by the formula (4), obtained in Example 1 was added to prepare the fragrance composition of Example 4.

The fragrance of the obtained fragrance composition of Example 4 was evaluated by a flavorist and was verified to be an apricot-type fragrance having light, gorgeous floweriness and sweetness.

TABLE 1

| Ingredients | parts by mass |
| --- | --- |
| Hexyl cinnamic aldehyde | 25 |
| Linalol | 20 |
| Ethyl brassylate | 15 |
| γ-Undecalactone | 10 |
| γ-Decalactone | 6 |
| Benzyl acetate | 5 |
| Diethyl malonate | 2 |
| β-Ionone | 2 |
| o-tert-Butyl acetate | 2 |
| cis-3-Hexenyl acetate | 1 |
| Limonene | 1 |
| γ-Nonalactone | 1 |
| Total | 90 |

Example 5

Fruit-Type Fragrance Composition

First, the fragrance composition (control substance) having the composition shown in Table 2 was prepared. Next, to 90 parts by mass of the control substance, 10 parts by mass of 2,4-dimethyl-bicyclo[2.2.2]octane-2-carboxylic acid ethyl ester represented by the formula (4), obtained in Example 1 was added to prepare the fragrance composition of Example 5.

The fragrance of the obtained fragrance composition of Example 5 was evaluated by a flavorist and was verified to be a fruit-type fragrance recalling the fresh and juicy feeling of an apple.

TABLE 2

| Ingredients | parts by mass |
| --- | --- |
| o-tert-Butylcyclohexyl acetate | 30 |
| Ethylene brassylate | 14 |
| Allyl heptanoate | 10 |
| Dimethylbenzylcarvinyl acetate | 10 |
| γ-Undecalactone | 10 |
| α-Ionone | 5 |
| Allyl cyclohexylpropionate | 2 |
| Amyl cinnamic aldehyde | 2 |
| Ethyl acetoacetate | 2 |

TABLE 2-continued

| Ingredients | parts by mass |
| --- | --- |
| Triplal (IFF trade name) | 2 |
| cis-3-Hexenol | 1 |
| cis-3-Hexenyl acetate | 1 |
| Limonene | 1 |
| Total | 90 |

INDUSTRIAL APPLICABILITY

As described above, the carboxylic acid ester compound represented by the general formula (1) of the present invention has an intense aroma provided both with a fruity aroma and with a spicy, rose-like floral feeling recalling damascone, and additionally is also comparatively excellent in aroma sustainability; hence the carboxylic acid ester compound is widely and effectively usable as a fragrance imparting component or a material for a compound fragrance in a broad range of fields, and is particularly effectively usable in applications, for example, in perfumery and cosmetics, health and sanitary materials, convenience goods, fiber, fiber products, clothing, food, quasi-pharmaceutical products and medicinal supplies. The carboxylic acid ester compound represented by the general formula (1) of the present invention has features such as bulky ring structure, rigidity, optical transparency, high Tg and lubricity (liposolubility) due to 2,4-dimethyl-bicyclo[2.2.2]octane, and is widely and effectively usable, as a raw material (inclusive of the intermediates in organic synthesis), for example, for medicines, agricultural chemicals, fragrances, functional resins, and optical functional materials and electronic functional materials.

The present application claims the priority of the Japanese Patent Application (Patent Application No. 2011-067952) filed Mar. 25, 2011, the contents of which are incorporated herein by reference.

The invention claimed is:

1. A carboxylic acid ester compound of formula (1):

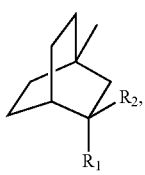

(1)

wherein one of $R_1$ and $R_2$ is a methyl group and the other of $R_1$ and $R_2$ is —COOR, wherein R is an alkyl group having 1 to 4 carbon atoms.

2. The carboxylic acid ester compound of claim 1, having formula (1a):

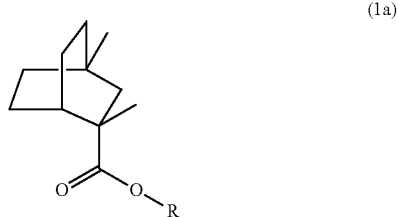

(1a)

wherein R is an alkyl group having 1 to 4 carbon atoms.

3. The carboxylic acid ester compound of claim 2, wherein, in formula (1a), R is a methyl group.

4. The carboxylic acid ester compound of claim 2, wherein, in formula (1a), R is an ethyl group.

5. The carboxylic acid ester compound of claim 2, wherein, in formula (1a), R is an n-propyl group.

6. The carboxylic acid ester compound of claim 2, wherein, in formula (1a), R is an iso-propyl group.

7. The carboxylic acid ester compound of claim 2, wherein, in formula (1a), R is an n-butyl group.

8. The carboxylic acid ester compound of claim 2, wherein, in formula (1a), R is an iso-butyl group.

9. The carboxylic acid ester compound of claim 2, wherein, in formula (1a), R is a tert-butyl group.

10. A fragrance composition, comprising the carboxylic acid ester compound of claim 1.

11. The fragrance composition of claim 10, wherein the content of the carboxylic acid ester compound is from 0.01 to 90% by mass, based on a total mass of the fragrance composition.

12. The fragrance composition of claim 10, wherein the content of the carboxylic acid ester compound is from 0.1 to 50% by mass, based on a total mass of the fragrance composition.

13. A method for producing the carboxylic acid ester compound of claim 1, the method comprising:

reacting 4-isopropenyl-1-methyl-1-cyclohexene represented by formula (2):

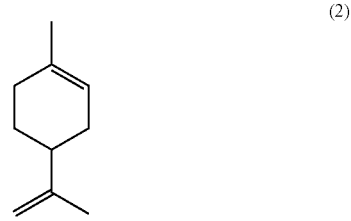

(2)

with carbon monoxide and a monovalent alcohol having 1 to 4 carbon atoms in the presence of hydrogen fluoride, thereby obtaining the carboxylic acid ester compound of formula (1):

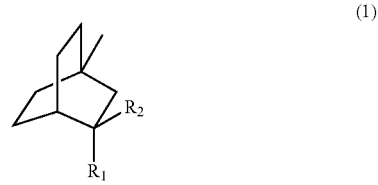

(1)

wherein one of $R_1$ and $R_2$ is a methyl group and the other of $R_1$ and $R_2$ is —COOR, wherein R is an alkyl group having 1 to 4 carbon atoms.

* * * * *